United States Patent [19]
Himmelstein et al.

[11] Patent Number: 5,599,534
[45] Date of Patent: Feb. 4, 1997

[54] REVERSIBLE GEL-FORMING COMPOSITION FOR SUSTAINED DELIVERY OF BIO-AFFECTING SUBSTANCES, AND METHOD OF USE

[75] Inventors: Kenneth J. Himmelstein, Omaha, Nebr.; Cara L. Baustian, Pearl River, N.Y.

[73] Assignee: University of Nebraska, Omaha, Nebr.

[21] Appl. No.: 287,694

[22] Filed: Aug. 9, 1994

(Under 37 CFR 1.47)

[51] Int. Cl.$^6$ .......................... A61K 31/74; A61K 31/19; A61K 47/38; A01N 25/04
[52] U.S. Cl. .................. 424/78.04; 424/427; 424/428; 514/912; 514/913; 514/914; 514/915
[58] Field of Search .................. 424/78.04, 427, 424/428; 514/912, 913, 914, 915

[56] References Cited

U.S. PATENT DOCUMENTS

| | | | |
|---|---|---|---|
| 4,188,373 | 2/1980 | Krezanoski et al. | 514/11 |
| 4,271,143 | 6/1981 | Schoenwald et al. | 514/9 |
| 4,407,792 | 10/1983 | Schoenwald et al. | 514/397 |
| 4,474,751 | 10/1984 | Haslam et al. | 514/11 |
| 4,474,752 | 10/1984 | Haslam et al. | 434/78 |
| 4,474,753 | 10/1984 | Haslam et al. | 424/78.06 |
| 5,252,318 | 10/1993 | Joshi et al. | 424/78.04 |
| 5,292,516 | 3/1994 | Viegas et al. | 424/423 |
| 5,292,517 | 3/1994 | Chang et al. | 424/426 |

OTHER PUBLICATIONS

Podder et al., (1992), Exp. Eye Res., 54: 747–757.
Schoenwald et al., (1978) J. Pharm. Sci., 67: 1280–1283.

*Primary Examiner*—Carlos Azpuru
*Attorney, Agent, or Firm*—Dann, Dorfman, Herrell and Skillman

[57] ABSTRACT

Reversibly gel-forming compositions for sustained delivery of bio-affecting substances are disclosed. The compositions exhibit significant changes in viscosity in response to changes in pH. The compositions contain relatively low concentrations of a stable combination of at least one pH-responsive gelling polymer and at least one other thermally nonresponsive polymer. The compositions are preferably formulated to include one or more therapeutic or diagnostic agents for administration as a liquid that will gel in situ or for topical application as a pre-formed gel.

22 Claims, 8 Drawing Sheets

REVERSIBLE GEL-FORMING COMPOSITION FOR SUSTAINED DELIVERY OF BIO-AFFECTING SUBSTANCES, AND METHOD OF USE

FIELD OF THE INVENTION

The present invention relates to compositions and methods for sustained delivery of bio-affecting substances, such as diagnostic or therapeutic agents. More particularly, the present invention is directed to reversibly-gelling drug delivery vehicles comprising an aqueous solution of polymers, at least one of which is transformed from a liquid to a gel form in response to changes in pH.

BACKGROUND OF THE INVENTION

Various methods and compositions have been proposed for efficient delivery of therapeutic and diagnostic agents to their sites of action. One difficulty in the administration of such agents is the necessity for the drugs to remain in contact with the target tissue for a sufficient period of time, at a sufficient concentration to achieve the desired therapeutic or diagnostic effect. Such difficulties are particularly pronounced for compounds that must be administered by topical application, especially to fluid-associated tissues such as ocular tissue, nasal mucosa or the oral cavity. To illustrate, conventional ocular delivery systems such as eye drops often result in low bioavailability and poor therapeutic response because high tear fluid turnover and dynamics result in rapid precorneal elimination of the compounds. An increase in dosing frequency or the use of highly concentrated solutions to increase bioavailability is undesirable due to poor patient compliance and/or the risk of toxicity resulting from the systemic absorption of the drug via the nasolacrimal duct. Similar difficulties are encountered in administration of topical agents to other fluid-associated surface tissues, such as the nasal mucosa or oral cavity.

To address the problems associated with ocular drug delivery, various ophthalmic vehicles, such as suspension, ointments and inserts, have been investigated in attempts to extend the ocular residence time of drugs for topical applications to the eye. Such compositions have been applied directly to the conjunctiva or cul-de-sac of the eye to facilitate sustained retention of pharmaceutical agents contained therein on the surface of the eye.

Although these ocular delivery systems offer some improvement over conventional ophthalmic solutions, they have received poor patient compliance as a result of eye irritation due to particulate matter in suspensions, blurred vision caused by ointments, discomfort due to crusting of gels and ointments around the eye and difficulties associated with the placement and removal of inserts in the eye.

Another disadvantage of semi-solid gels or ointments is the tendency for these compositions to migrate within the cul-de-sac or to be lost from the eye. Additionally, such gels or ointments often persist in the ocular environment past the point at which all of the pharmaceutical compound has been delivered, thereby continuing to cause undesirable side effects such as crusting of the material and blurred vision.

Thus, from the point of view of patient compliance, a liquid ocular delivery system is most acceptable due to its ease of administration compared to the semi-solid gels and ointments described above. However, conventional liquid delivery systems are incapable of achieving the extended surface contact for sustained delivery of the diagnostic or therapeutic agent.

One approach to increasing the residence time of topically-applied drugs while enabling administration of the drugs in liquid form has been to develop delivery systems based on the concept of in situ gel formation. These delivery systems are made from polymers that exhibit phase transitions due to physico-chemical changes in their microenvironments. They can be instilled as liquid drops into the cul-de-sac of the eye, for example, where the microenvironment of the eye transforms the polymers into a gel or semi-solid phase. Similarly, liquid forms of the delivery systems can be introduced into the nasal mucosa, oral cavity or other physiological environment, wherein they would transform into a gel. Sustained release of ophthalmic drugs has been reported from gels and polymer matrices, and improved bioavailability and patient response to therapeutic agents has been shown in many cases. For example, Schoenwald et al., J. Pharm. Sci., 67: 1280–1283 (1978), showed that aqueous Carbopol® gels administered into rabbit eyes were retained for 4–6 hours and resulted in longer duration of action of incorporated pilocarpine compared to a viscous solution preparation (see also U.S. Pat. Nos. 4,271,143 and 4,407,792).

Subsequently, numerous in situ gel-forming delivery vehicles have been disclosed, which are based in changes in physico-chemical structure as a result of variations in temperature, pH, ionic strength, or a combination thereof. In U.S. Pat. No. 4,188,373, for example, a gel-forming drug delivery system is disclosed which utilizes proprietary nonionic difunctional polyoxyalkyene derivatives of propylene glycol (known as Pluronic® polyols) as a thermally gelling polymer. The desired sol-gel transition temperature is said to be obtained by appropriate adjustment of the polymer concentration. Another thermally triggered system is disclosed in U.S. Pat. No. 4,474,751 and 4,474,752, which disclose an aqueous drug delivery system, based on proprietary nonionic tetrafunctional polyoxyalkylene derivatives of ethylene diamine (known as Tetronic® polyols), which gel at temperatures from about 30°–100° C. The sol-gel transition temperature and rigidity of these gels are said to be capable of adjustment by changes in polymer concentration combined with the pH and ionic strength of the solution. These compounds contain from about 10% to about 50% by weight of Tetronic® polymers. Because of the adjustments to the solutions that must be made in order to produce a compound which sets at a physiologically useful temperature, the available viscosity range of such gelled products is limited.

As an alternative, in situ gel-forming compositions have been developed which gel in response to changes in pH. For example, U.S. Pat. No. 5,292,517 discloses a pH sensitive, reversible gelling copolymeric drug delivery system, which comprises an aqueous solution containing up to 25% (w/v) of poly (methylvinylether)/maleic acid) as the pH-sensitive gelling copolymer. These compositions are said to exhibit a sol-gel transition over physiologically compatible pH ranges.

Although successful in achieving increased drug retention times, the relatively high polymer concentration utilized in such thermally- or pH-sensitive gelling formulations undesirably increases the buffering capacity and the thermal energy needed to induce gelation of those formulations, leading to irritation and discomfort when used in the eye or other physiological target tissue. Moreover, the use of such high polymer concentrations is costly, and can retard the gelling process in situ, which can result in loss of the pharmaceutical agent from the site of administration during the lengthy time in which gelling occurs.

Addressing the difficulties associated with reversibly gelling compositions containing high concentrations of the gelling polymer, U.S. Pat. No. 5,252,318 discloses a reversibly gelling composition having a lower polymer concentration, which exhibits a sol-gel transition in response to simultaneous variation in two physical parameters, such as temperature and pH. The use of a combined polymer system that reversibly gels in response to two or more physicochemical parameters is said to enable the formulation of in situ gelling compositions having a significantly reduced polymer concentration. While the reduction in polymer concentration solves the problems associated with high polymer concentration, the requirement for a composition that gels in response to simultaneous variations in at least two physical parameters limits the flexibility of formulating in situ gel-forming compositions, inasmuch as they must contain at least one pH-sensitive polymer and at least one thermally sensitive polymer.

Accordingly, a distinct advantage would be obtained by providing a reversibly gelling drug delivery composition comprising an aqueous solution of polymers at sufficiently low concentration to avoid the undesirable effects of high buffering capacity and slow induction of gelation, but which is not dependent on two independent physico-chemical parameters to achieve that result. Such a composition would retain the advantages of the two-parameter reversible gelling compositions described above, but would also enable greater flexibility in formulating in situ gelling compositions for delivery of a wide variety of diagnostic and therapeutic agents.

SUMMARY OF THE INVENTION

The present invention provides a reversibly-gelling composition for sustained delivery of therapeutic or diagnostic agents that can be formulated at a low polymer concentration, yet relies on only one physico-chemical parameter for its reversibly-gelling characteristic. The composition, which exhibits the property of reversible gelation in response to variation in pH over a pre-determined range, comprises an aqueous solution that includes about 0.01% to 10.0% (w/w) of at least one pharmaceutically acceptable pH-responsive gelling polymer and about 0.01% to 30.0% (w/w) of at least one other pharmaceutically acceptable polymer. Previously, it had been believed that a reversibly gelling composition could not be produced with such a low concentration of polymers unless a multiple gelation triggering mechanism (i.e., substantially simultaneous changes in pH and temperature) were employed. In accordance with the present invention, it was surprisingly discovered that superior reversibly-gelling compositions can be formulated at low polymer concentration using two or more compatible polymers, one of which is sensitive to changes in pH, the others of which need not be sensitive to changes in temperature.

According to one aspect of the invention, the above-described composition exhibits a reversible change in viscosity in response to increasing pH. The pH-sensitive gelling polymer of these compositions contains acidic groups, and is preferably a polymer of acrylic acid or derivatives thereof. According to another aspect of the invention, the above-described compositions exhibit a reversible change in viscosity in response to decreasing pH. The pH-sensitive gelling polymers of these compositions contain basic groups, and preferably are polymers having weakly-pendant amino groups. The second polymeric component of either the acidic or basic gelling compositions of the invention comprises a pharmaceutically acceptable water-soluble polymer that need not rely on changes in pH or temperature for its contribution to the reversible gelation of the composition and need not be capable of gelation on its own. This polymeric component is compatible with the pH-responsive polymer, such that a clear solution of the composition is obtained at pH of formation (i.e., low pH for acidic compositions and high pH for basic compositions). In a preferred embodiment, the polymer is a thermally insensitive hydroxyalkyl cellulose.

According to another aspect of the invention, a pharmaceutical composition is provided that includes a pH-sensitive reversibly gelling drug delivery vehicle as described above and an effective amount of a therapeutic or diagnostic agent. Additionally, methods are provided for sustained delivery of a therapeutic or diagnostic agent to a patient. Such methods comprise administering a pharmaceutical composition that includes an effective amount of the therapeutic or diagnostic agent disposed within a pH-sensitive reversibly gelling drug delivery vehicle as described above.

The reversible gel-forming properties of the compositions of the invention make them well suited for sustained delivery of a wide variety of therapeutic and diagnostic agents via topical application, particularly to mucosa and other fluid-associated or physically inaccessible tissues such as eyes, ears, the oral and nasal cavity and similar physiological environments. Additionally, the gel-forming delivery vehicle and its methods of use in accordance with the present invention offer a notable advantage over in situ gel-forming drug delivery systems and methods of the prior art. For instance, the reversible gelling compositions of the invention contain comparatively low concentrations of polymeric components, the lowered buffering capacity and thermal gelation threshold obtained thereby resulting in rapid formation of superior gels in situ and the minimization of patient discomfort resulting from exposure of tissues to pH extremes for extended periods, the low polymer concentration also reducing the cost of producing such compositions. Moreover, these advantageous features are accomplished through a polymeric formulation, the gelation of which is triggered by only one physico-chemical parameter (i.e., change in pH). This feature of the compositions of the invention enables a broad range of polymeric components to be utilized, thereby enabling greater flexibility in the formulation of sustained release drug delivery vehicles for a variety of applications.

Additional advantages and features of the present invention will be apparent to those skilled in the art from the Detailed Description of the Invention set forth below, considered in conjunction with the accompanying drawings.

DETAILED DESCRIPTION OF THE INVENTION

Figure 1:
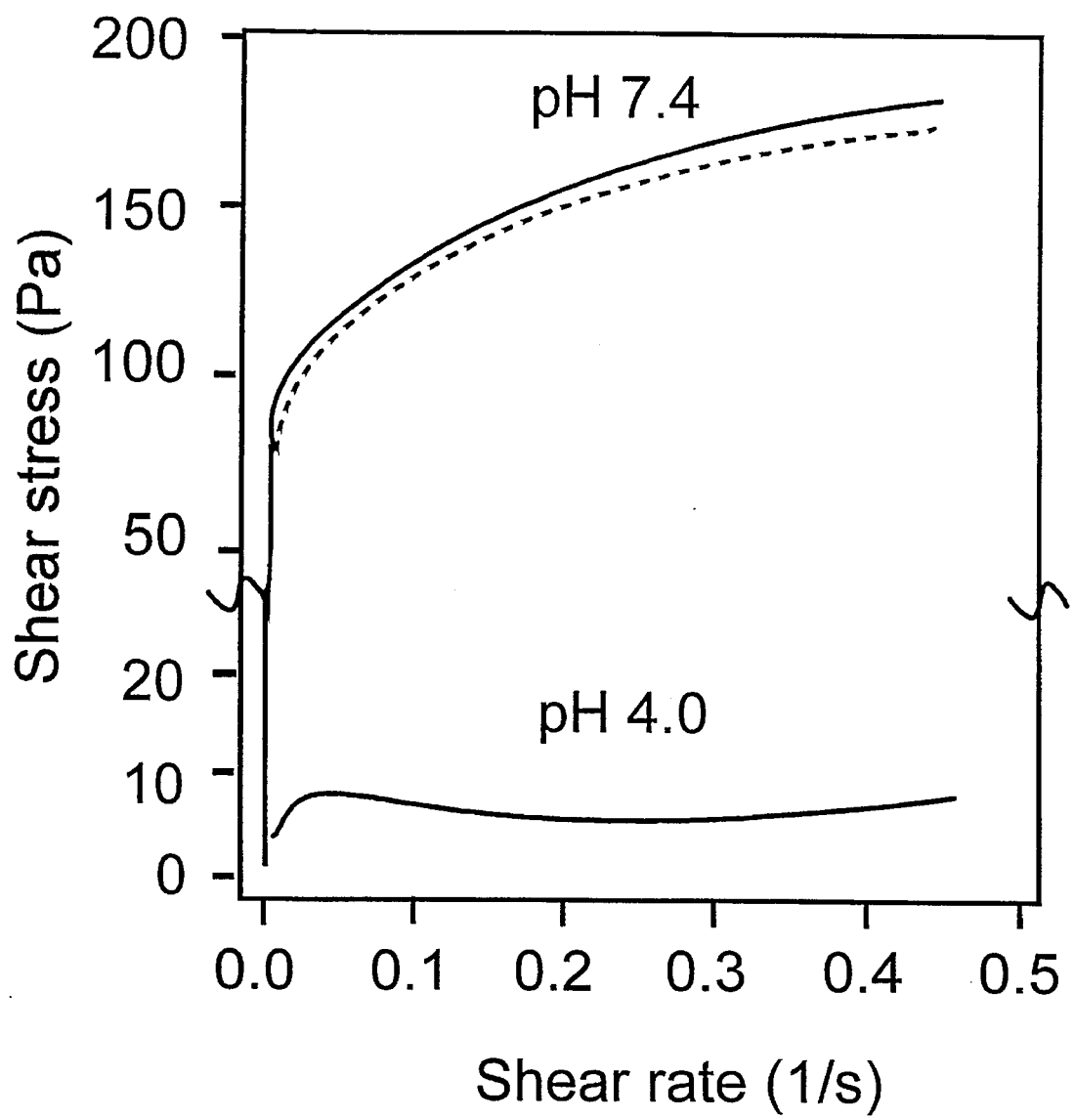
FIG. 1. Shear stress vs. shear rate flow curves of 1.5% hydroxypropylmethylcellulose (HPMC), 0.3% Carbopol aqueous solution at pH 4.0 and 7.4. The measurements at 25° C. are represented by dashed lines and that at 37° C. by a solid line.

The present invention provides a pH-responsive reversibly gelling composition for sustained delivery of therapeutic or diagnostic agents, and uses thereof in formulation and administration of pharmaceutical compositions containing such therapeutic or diagnostic agents. These compositions exhibit a sol-gel transition over physiologically compatible pH ranges. In the liquid form, the compositions are composed of a clear, free-flowing physiologically compatible solution. Upon exposure to a pre-determined variation in pH, the compositions rapidly increase in viscosity by over an order of magnitude to a highly viscous gel-like consistency, which is optically clear, lubricating and slowly-dissolving. These properties make the reversibly gelling compositions of the invention suitable for use as drop- or spray-instillable or topical drug delivery vehicles. The compositions are particularly suitable for delivering pharmaceutical compounds to the ocular environment due to the clarity and lubricating properties of the gel.

The compositions of the invention are unique from those disclosed in the prior art in that they possess the above-described clarity and rapid gelation response to changes in pH, yet contain very small polymer concentrations, as compared with pH-sensitive reversible gelation systems heretofore available. Although reversibly gelling compositions of low polymer concentration have been disclosed, (U.S. Pat. No. 5,252,318) it has been taught that a composition having the desirable gelling properties described hereinabove required the use of two or more polymers, one of which exhibits thermally-responsive gelation, while the other polymer exhibits pH-responsive gelation. In accordance with the present invention, and contrary to the teachings of the prior art, it has now been discovered that a low-concentration reversibly-gelling compositions can be formulated without the requirement for inclusion of a temperature-sensitive gelling polymer. Thus, compositions may be formulated which exhibit reversible gelation in response to variations in pH only, yet the polymer concentrations can be kept very low. Such compositions retain the advantage of being lower in cost, having a substantially reduced buffering capacity and rapid gelation at the sol-gel transition, and possess the added advantage of enabling an additional range of polymers (i.e., thermally nonresponsive polymers) to be employed in formulating sustained delivery pharmaceutical compositions.

An example of a reversibly-gelling composition of the invention which exhibits an increase in viscosity in response to variation in pH over a pre-determined range comprises an aqueous solution that includes a stable combination of at least one pharmaceutically acceptable pH-responsive gelling polymer and at least one other pharmaceutically acceptable, thermally nonresponsive polymer in amounts sufficient to produce the reversible change in pH over the pre-determined pH range. As used herein with reference to the components of the gel-forming composition and pharmaceutical formulations of the invention, the expression "pharmaceutically acceptable" refers to substances which do not adversely affect the activity or efficacy of the therapeutic or diagnostic agent or agents included in the reversibly gelling delivery composition, and which are not in themselves toxic to the recipient. With reference to the polymers comprising the gel-forming composition of the invention, the expression "pH-responsive" refers to polymers which exhibit the property of reversible gelation in response to a change, either an increase or a decrease, in pH over a pre-determined range. Similarly, the expressions "thermally responsive/non-responsive" refers to polymers which do/do not exhibit the property of gelation in response to a change in temperature, although, as will be appreciated by those skilled in the art, other characteristics of a gelatinous composition may be affected or modified by temperature.

Preferred exemplary compositions of the invention undergo an increase in viscosity in response to increasing pH over a pre-determined range, preferably in a physiological range between about pH 2.5 and pH 7.5. Depending on polymer type, polymer concentration, temperature, ionic strength, shear rate and similar factors, the change in viscosity will range from about 200 cP to about 1,000,000 cP in response to variation between about 2.5 and 7.5. Preferred pH-responsive gelling polymers exhibiting increased viscosity in response to increasing pH include, but are not limited to: linear, branched or cross-linked acidic polymers, especially carboxylic acid-containing polymers, and particularly carboxyvinyl polymers of monomers of acrylic acid and alkyl or cycloalkyl acrylic acids such as methacrylic acid, ethacrylic acid, β-methacrylic acid and α-cyclohexacyclic acid; as well as arylacrylic acids such as α-phenylacrylic acid and α-benzylacrylic acid. and alkylcrotonic acids such as cis-α-methylcrotonic acid, trans-α-methylcrotonic acid, α-butylcrotonic acid, and the like. These pH-sensitive polyacids are incorporated into compositions of the invention at a concentration of between 0.01% to 10.0% (w/w), with preferred concentrations of 0.05% to 2.0% (w/w).

Other exemplary compositions of the invention undergo an increase in viscosity in response to decreasing pH over a pre-determined range. Preferred pH-responsive gelling polymers that increase viscosity with decreasing pH include, but are not limited to: linear, branched, or cross-linked basic polymers, including amino derivatives of polyacrylate and polyalkylacrylates, such as poly-N-N-dimethylaminoethylmethacrylate, and other polymers containing weakly basic pendant groups. These polymers are incorporated into compositions of the invention at a concentration of 0.01% to 10.0% (w/w), and preferably from 0.05% to 2.0% (w/w). Compositions of the invention containing such pH-responsive polymers exhibit an increase in viscosity from about 200 cP to 1,000,000 cP in response to variations in pH ranging from about pH 9.0 to pH 6.0.

To achieve the desired gelation properties at low polymer concentration, compositions of the invention comprise at least one other pharmaceutically acceptable polymer that is capable of combining or admixing with the pH-responsive polymers to impart the desired rheological properties to the compositions of the invention in both the soluble form and the gel-like form. Preferred polymers for use in this capacity include, but are not limited to, various thermally nonresponsive cellulose derivatives, such as certain alkyl celluloses, hydroxyalkyl celluloses and cellulosic ethers. Particularly preferred is hydroxypropylmethylcellulose (HPMC) at a concentration of about 0.01% to 20.0% (w/w), with 0.05% to 5.0% (w/w) being particularly preferred. Thermally responsive cellulose derivatives have previously been disclosed to be synergistic in gel formation with certain of the pH-responsive polymers described above, a feature which previously was thought to be primarily associated with the temperature sensitivity of these polymers. However, in accordance with the present invention, it has been discovered that thermally nonresponsive cellulose derivatives, particularly HPMC, also exhibit the same synergism, inasmuch as mixtures of such polymers and the pH-responsive polymers in accordance with the invention exhibit viscosities substantially greater than the sum of the individual viscosities of the individual aqueous polymer solutions. This unique feature of thermally non-responsive cellulose derivatives, along with their visco-elastic stability over a wide range of pH from approximately 3 to 11 makes them particularly suitable as the additional polymeric component of the compositions of the invention.

A preferred exemplary composition of the invention thus comprises a homogenous association of hydroxypropylmethylcellulose and a cross-linked polyacrylic acid, such as Carbopol 974P NF, a hydrophilic acrylic polymer available from the B. F. Goodrich Company. These polymers are preferably incorporated into an aqueous solution at concentrations ranging from 0.01% to 10.0% (w/w) Carbopol and from 0.01% to 20.0% (w/w) HPMC, preferably with Carbopol concentrations of 0.05% to 2.0% and HPMC concentrations of 0.05% to 5.0%, and most preferably at a Carbopol concentration of 0.3% and an HPMC concentration of 1.5%. It will be appreciated by those of skill in the art that varying the concentration ranges of the preferred composition results in a wide variety of viscosities and sol-gel transition pHs.

The compositions of the invention can be formulated at a variety of pHs, and it is contemplated that such formulations may include pHs at which the compositions are in flowable liquid form, or pHs at which the compositions are in gel form. The flowable liquid forms of the composition are particularly useful for pharmaceutical formulations to be applied by drops (e.g., eye drops) or sprays (e.g., nasal sprays), and the like, while the gel form of the composition are suitable for topical administration of pharmaceutical compounds, such as administration on the surface of the skin.

The osmolality of the compositions of the invention may be adjusted to suit the physiological environment into which the composition is to be introduced. The osmolality can be adjusted through the addition of physiologically acceptable salts or non-ionic supplements, including sodium chloride, potassium chloride, magnesium chloride, sodium lactate, magnesium phosphate, mannitol, sucrose, glycerine, and the like. Additionally, if desired, the compositions of the invention may also contain other preservatives or additives. Suitable water-soluble preservatives include sodium bisulfite, sodium thiosulfate, ascorbate, benzalkonium chloride, chlorobutanol, thimerosal, phenylmercuric, borate, parabens, benzylalcohol and phenylethanol. These agents may be present, generally, in amounts of about 0.001% to about 5% by weight and, preferably, in the amount of about 0.01 to about 2%.

In addition to being useful for adjusting osmolality, the viscosity of the aqueous compositions of the invention can be modified by the addition of a pharmaceutically acceptable salt, such as a mono- or divalent salt, including sodium chloride, potassium chloride, calcium chloride, or mixtures thereof, as well as suitable alkali metal salts such as sodium sulfate. The ratio of salt to combined polymer in the solution should range from 0 to about 0.5, and preferably from about 0.045 to 0.075. The addition of salt tends to lower the viscosity of the aqueous polymer composition and thus can be used for fine adjustments of viscosity in the formulation of various pharmaceutical compositions.

The pH-responsive reversibly gelling compositions of the invention may be utilized as wetting agents or lubricants without the addition of a therapeutic or diagnostic agent. However, it is contemplated that the more significant utility of the compositions of the invention will be as sustained delivery vehicles for administering therapeutic or diagnostic compounds.

The drug delivery pharmaceutical compositions of the invention may be formulated as aqueous solutions or as gels, and are therefore suitable for utilization in a wide variety of physiological applications, such as ocular, oral, otic, nasal, topical (epidermal), rectal, vaginal or intraurinary administration of pharmaceutical compounds. Accordingly, a pharmaceutical composition of the invention will contain, based on the total weight of the composition, and effective amount of one or more therapeutic or diagnostic agents, typically from about 0.0001% to 50% by weight therapeutic or diagnostic agent. Depending upon the condition of the patient, the above-stated amounts may be varied to increase or decrease the dosage schedule, as appropriate. As used herein, the term "therapeutic agent" refers to a substance used in treating or ameliorating a disease or a medical condition. The term "diagnostic agent" refers to a substance used in diagnosing the nature of a disease or medical condition, or some aspect thereof. The term "patient" refers to the subject having the disease or medical condition being treated or diagnosed, and is intended to include humans and animals.

Virtually any therapeutic agent or diagnostic agent capable of administration using the various in situ gelling compositions of the prior art can be administered using the sustained-release compositions of the present invention. Particularly preferred are therapeutic and diagnostic agents which exhibit poor bioavailability, including timolol, betaxalol, levobunolol, pilocarpine, dipivefrin, and the like. Other therapeutic and diagnostic agents that can be administered by the sustained-delivery compositions of the present invention include, but are not limited to:

(1) analgesics such as aspirin, acetaminophen, diflusinal and the like;

(2) antibacterial substances such as beta-lactam antibiotics, including cefoxitin, n-formamidoyl-thienamycin and other thienamycin derivatives, tetracyclines, chloramphenicol, neomycin, carbenicillin, colistin, penicillin G, polymyxin B, vancomycin, cefazolin, cephaloridine, chibrorifamycin, gramicidin, bacitracin, sulfonamides; aminoglycoside antibiotics such as gentamycin, kanamycin, amikacin, sisomicin and tobramycin; nalidixic acid and analogs such as norfloxacin and the antimicrobial combination of flucalanine/pentizodone; nitrofurazones, and the like;

(3) antihistaminics and decongestants such as pyrilamine, chlorpheniramine, tetrahydrazoline, antazonline, and the like;

(4) antiathsma drugs such as theophylline, ephedrine, beclomethasone diproprionate, epinephrine and the like;

(5) anti-inflammatories and anti-arthritics such as cortisone, hydrocortisone, hydrocortisone acetate, betamethasone, dexamethasone, dexamethasone sodium phosphate, preunisone, methylpredinisolone, medrysone, fluorometholone, fluocortolone, preunisolone, preunisolone sodium phosphate, triamcinolone, phenylbutazone, ibuprofen, indomethacin, sulindac, its salts and its corresponding sulfide, and the like;

(6) miotics and anticholinergics such as echothiophate, pilocarpine, physostigmine salicylate, diisopropylfluorophosphate, epinephrine, dipivolyl epinephraine, neostigmine, echothiophate iodide, demecarium bromide, carbachol, methacholine, bethanechol, and the like;

(7) mydriatics such as atropine, homatropine, scopolamine, hydroxyamphetamine, ephedrine, cocaine, tropicamide, phenylephrine, cyclopentolate, oxyphenonium, eucatropine, and the like; and other medicaments used in the treatment of eye conditions or diseases, such as (9) antiglaucoma drugs, for example, betaxalol, pilocarpine, timolol, especially as the maleate salt and R-timolol and a combination of timolol or R-timolol with pilocarpine, as well as epinephrine and epinephrine complex or prodrugs such as the bitartrate, borate, hydrochloride and dipivefrin derivatives and hyperosmotic agents such as glycerol, mannitol and urea;

(10) antiparasitic compounds and/or anti-protozoal compounds such as ivermectin; pyrimethamine, trisulfapyrimidine, clindamycin and corticosteroid preparations;

(11) antiviral effective compounds such as acyclovir, 5-lodo-2'-deoxyuridine (IDU), adenosine arabinoside (Ara-A), trifluorothymidine and interferon and interferon inducing agents such as Poly I:C;

(12) urinary tract disinfectives such as sulfamethoxyazole, trimethoprim, nitrofurantoin, norfloxacin and the like;

(13) anticoagulants such as heparin, bishydroxy coumarin, warfarin and the like;

(14) anticonvulsants such as diphenylhydantoin, diazepan and the like;

(15) antidepressants such as amitriptyline, chlordiazepoxide, perphenazine, protriptyline, imipramine, doxepin and the like;

(16) antidiabetics such as insulin, tolbutamide, somatostatin and its analogs, tolazanide, acetohexamide, chlorpropamide and the like;

(17) antipsychotics such as prochlorperazine, lithium carbonate, lithium citrate, thioridazine, molindone, fluphenazine, trifluoperazine, perphenazine, amitriptyline, triflupromazine and the like;

(18) antihypertensives such as spironolactone, methyldopa, hydralazine, clonidine, chlorothiazide, deserpidine, timolol, propranolol, metopropol, prazosin hydrochloride, reserpine and the like;

(19) muscle relaxants such as succinylcholine chloride, danbrolene, cyclobenzaprine, methocarbomol, diazepam and the like;

(20) carbonic anhydrase inhibitors such as acetazotamide, dichlorphenamide, 2-(p-hydroxyphenyl)thio-5-thiophenesulfonamide, 6-hydroxy-2-benzothiazolesulfonamide and 6-pivaloyloxy-2-benzothiazolesulfonamide;

(21) anti-fungal agents such as amphotericin B, nystatin, flucytosine, natamycin, and miconazole;

(22) anesthetic agents such as etidocaine cocaine, henoxinate, dibucaine hydrochloride, dyclonine hydrochloride, naepaine, phenacaine hydrochloride, piperocaine, proparacaine hydrochloride, tetracaine hydrochloride, hexylcaine, bupivacaine, lidocaine, mepivacaine and prilocaine;

(23) ophthalmic diagnostic agents such as
  (a) those used to examine the retina and chloride-sodium fluorescein;
  (b) those used to examine the conjunctive, cornea and lacrimal apparatus such as fluorescein and rose bengal; and
  (c) those used to examine abnormal pupillary responses such as methacholine, cocaine, adrenaline, atropine, hydroxyamphetamine and pilocarpine;

(24) ophthalmic agents used as adjuncts in surgery such as alphachymotrypsin and hyaluronidase;

(25) chelating agents such as ethylenediamine tetraacetate (EDTA) and deferoxamine;

(26) immunosuppressive agents, antineoplastics and antimetabolites such as adriamycin, fluorouracil, asparaginase, methotrexate, cyclophosphamide, 6-mercaptopurine, azathioprine and the like;

(27) peptides and proteins such as atrial natriuretic factor, calcitonin-gene related factor, lutinizing hormone, releasing hormone, neuroterisin, vasoactive intestinal peptide, vasopressin, cyclosporine, interferon, substance P enkephalins, epidermal growth factor, eye derived growth factor, fibronectin, insulin-like growth factor and mesodermal growth factor;

(28) nucleic acids, such as oligonucleotides, DNA fragments and the like; and

(29) lubricating agents such as sodium hyaluronate or polyvinyl alcohol;

(30) combinations of the above such as antibiotic/anti-inflammatory as in neomycin sulfate-dexamethasone sodium phosphate, concomittant anti-glaucoma therapy such as timolol/maleate-aceclidine.

Representative diagnostic agents that may be incorporated in the drug delivery vehicle of the present invention include contrast agents, dyes and radiotracers, as well as biological molecules, such as antibodies, oligonucleotides and various ligands, alone or conjugated to detectable substances such as fluorescent compounds, dyes and enzymes.

The foregoing list of suitable bio-affecting agents is exemplary only and is not intended to limit the scope of the present invention. Additionally, it is also contemplated as being within the scope of the invention to incorporate insoluble or erodible microparticulate drug delivery systems known in the art into the compositions of the invention. Controlled release drug delivery systems can thus be incorporated into the compositions of the invention and retained at the site of administration for particularly effective bioavailability and sustained release.

Gelation of pharmaceutical compositions of the invention will cause the therapeutic or diagnostic agents included therein to become incorporated into the gelled polymer matrix, which will remain at the site of administration for sustained bioavailability and delivery as the gel slowly erodes and the therapeutic or diagnostic agents diffuse into the surrounding physiological environment. Along these lines it will be appreciated by those skilled in the art that varying the concentration of pharmaceutical agents within the composition will enable modification and control of the quantity of pharmaceutical compound delivered by dropable application, spray or topical administration. For example, a liquid drug delivery vehicle can be prepared in accordance with the present invention containing from about 0.0001 to about 50%, preferably about 0.01% to 20.0% by weight of a therapeutic agent, as previously noted. For drop instillation, the drop size will preferably range from approximately 20 µl to 50 µl with 25 µl drops being particularly preferred. Accordingly, one drop of the liquid composition, which comprises about 25 µl of solution, would preferably contain approximately 0.0025 mg to approximately 1.25 mg of pharmaceutical agent. Such an aqueous liquid drug delivery vehicle can easily be modified for administration as an atomized spray or vapor. de The following examples are provided to describe the invention in further detail. These examples are intended merely to illustrate specific embodiments of the reversibly-gelling compositions of the invention and should in no way be construed as limiting the invention.

EXAMPLE 1

Preparation of Reversibly-Gelling Drug Delivery Compositions and Determination of Rheological Properties

MATERIALS AND METHODS

Polyacrylic acid is available as Carbopol® (974P NF) from B. F. Goodrich, Cleveland, Ohio. Hydroxypropyl methylcellulose (HPMC) of three different average molecular weight grades (MW=26 kDa; MW=86 kDa; and MW=246 kDa) is available from the Dow Chemical Company, Midland, Mich. Unless otherwise specified HPMC of MW=86 kDa was used in the preparation of polymer solutions. Sodium hydroxide was purchased from J. T. Baker.

Aqueous solutions of 4.0% w/w HPMC were prepared by gradually adding weighed quantities polymer to 1/3rd of the required distilled, deionized water preheated to 90° C., with constant stirring. The final volume was made up by adding water cooled to 5° C. 1.0% w/w Carbopol solutions were prepared by dispersing the required amount in distilled, deionized water. All experiments were carried out using the same batch of prepared solutions. Solutions containing both HPMC and Carbopol were prepared by adding appropriately weighed amounts of the 4.0% HPMC and 1.0% Carbopol solutions. The resulting solutions were thoroughly mixed and equilibrated. The pH of the same were then adjusted to either 4.0±0.1 or 7.4±0.2 by addition of measured volumes of a 0.5M sodium hydroxide solution based on a titration curve for Carbopol. Finally, the desired w/w % concentrations were made by adding required volumes of distilled, deionized water to the samples. The samples were allowed to equilibrate for 48 hrs at room temperature prior to the evaluation of their rheological properties.

The rheological studies of the samples were carried out on a Haake viscometer (RV20, CV20, RC20) using a cone (4°) and plate geometry. The temperature was maintained to within ±0.1° C. by a Haake recirculating bath connected to the viscometer. The viscosity ($\eta$) and shear stress ($\tau$) of the polymer solutions of different compositions were measured as a function of shear rate (D) at 25° C. and 37° C. A typical run comprised a shear rate change from 0 to 0.5 $s^{-1}$ at a shear rate ramp speed of 0.05 $s^{-1}$/min, a 0.1 min wait at 0.5 $s^{-1}$, and finally a shear rate decrease to O $s^{-1}$ at the same ramp speed. The samples were equilibrated at the run temperature on the plate for 5 minutes prior to the analysis.

RESULTS

Aqueous solutions of different compositions containing HPMC and Carbopol were prepared and their rheological properties were studied. FIG. 1 shows the shear stress vs. shear rate ($\tau$ vs. D) flow curves for aqueous solutions containing 1.5% HPMC and 0.3% Carbopol at different conditions of pH and temperature. All solutions demonstrate a pseudoplastic $\tau$ vs. D flow curve with a yield point, indicating a plastic behavior. The solution at pH 4.0 and 25° C. has low shear stress and yield point. Upon increasing the pH to 7.4, there is significant increase in the shear stress and yield point value. An increase in temperature from 25° to 37° C. along with the increase in pH does not affect yield point and shear stress.

Figure 2:
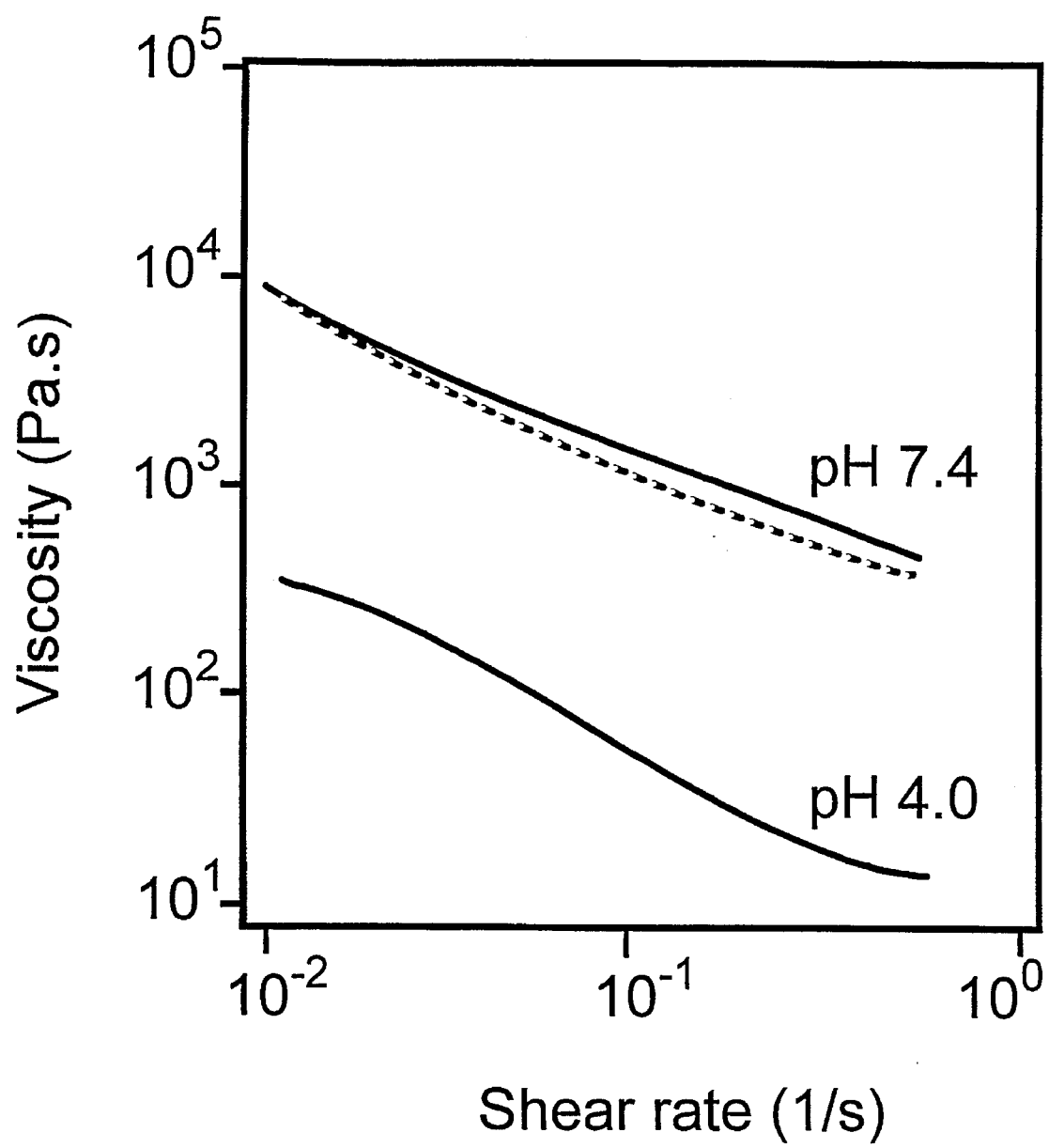
FIG. 2. Log viscosity vs. log shear rate profiles of 1.5% HPMC, 0.3% Carbopol aqueous solution at pH 4.0 and 7.4. The measurements at 25° C. are represented by dashed lines and that at 37° C. by a solid line.

FIG. 2 is a plot of log viscosity vs. log shear rate (log$\eta$ vs. logD) for the 1.5% HPMC, 0.3% Carbopol aqueous solutions under the same conditions of pH and temperature as in FIG. 1. The solution at pH 4.0 and 25° C. shows low viscosity. On increasing the pH from 4.0 to 7.4, the solution transforms from a sol to a stiff gel. Both the solutions at pH 7.4, one maintained at 25° C. and the other at 37° C., demonstrate log$\eta$ vs. logD profiles that are much higher in magnitude than the solution at pH 4.0 and 25° C. For purposes of comparison, log$\eta$ vs. logD and $\tau$ vs. D plots, respectively, were generated for a temperature/pH-triggered aqueous gelling system containing 1.5% methyl cellulose (MC; Sigma Chemical Co., St. Louis, Mo.) and 0.3% Carbopol, prepared by the same method as described for HPMC-Carbopol. Compared to the HPMC-Carbopol Carbopol system shown in FIGS. 1 and 2, the MC-Carbopol system showed a similar increase in viscosity, shear stress and yield point values as the pH is increased from 4.0 to 7.4. However, unlike the HPMC-Carbopol system, a simultaneous increase in temperature from 25° to 37° C. along with the pH change results in a further increment in the values of viscosity, shear stress, and yield point. However, these temperature mediated rheological changes in the MC-Carbopol system were temporary and were seen only at low shear rates. As the shear rate was increased, it was seen that the log$\eta$ vs. logD curve and the $\tau$ vs. D flow curve of the solution at pH 7.4 and 37° C. approached and ultimately coincided with that of the solution at pH 7.4 and 25° C. Following instillation of an ophthalmic delivery system prepared using the MC-Carbopol system in the cul-de-sac of the eye, it is likely to encounter shear forces at rates higher than 0.5 $s^{-1}$ examined in the experiment. Thus, it appears that the in situ gelation of the delivery system will occur as a result of the pH effect with little or no contribution of the temperature related phase transition observed in the in vitro experiments.

These rheological properties of the Carbopol-HPMC aqueous system are indicative of its utility as an in situ gel forming delivery system for ophthalmic and other applications. The delivery system can be formulated to be a liquid at a specific pH which can be instilled into the eyes as drops. Exposure to the physiological pH will induce a sol to gel phase transition to form a semisolid gel in sit.

A detailed study on the effects of changing the solution composition on the rheological properties was carried out.

Figure 3:
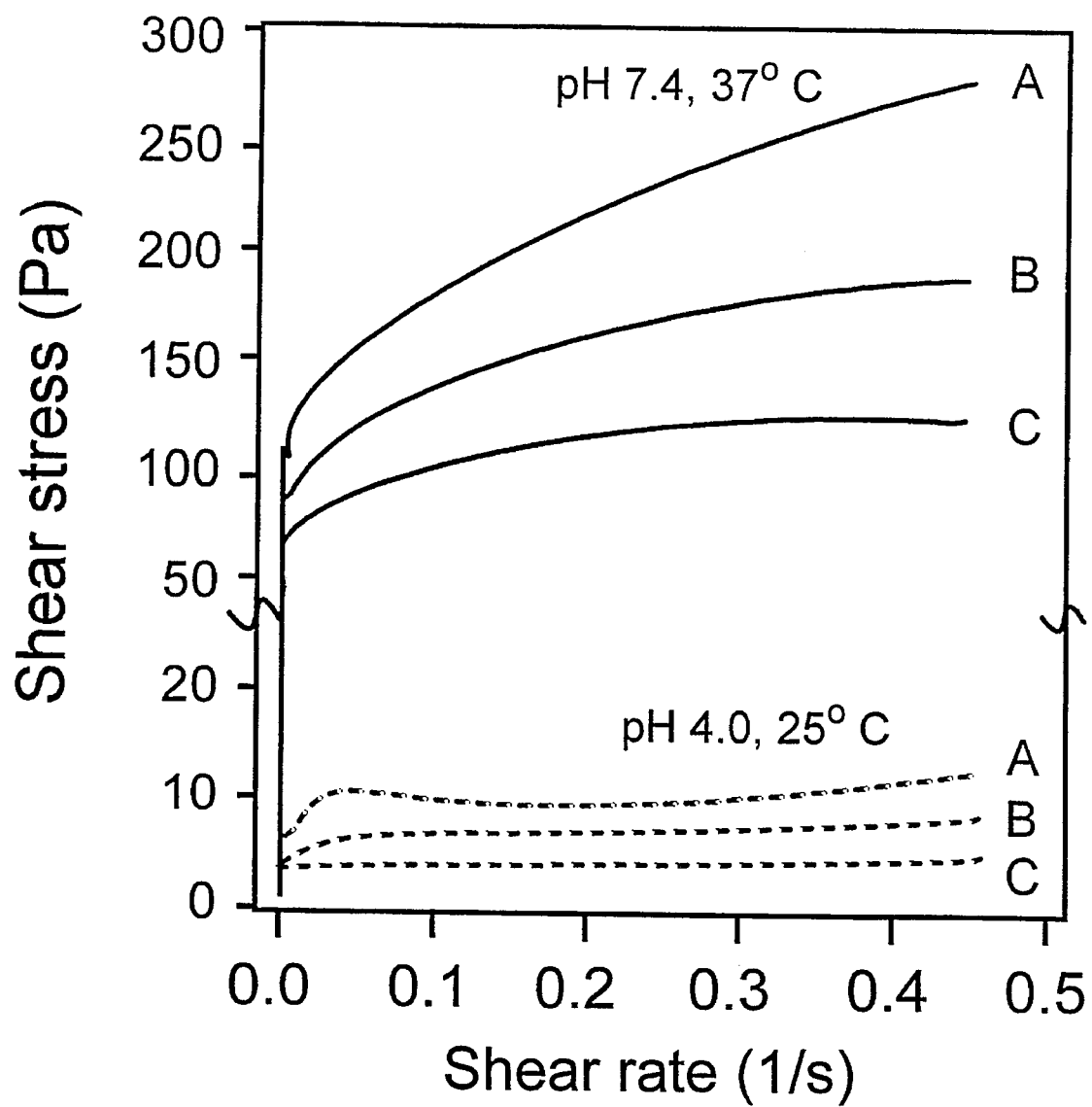
FIG. 3. Shear stress vs. shear rate flow curves of aqueous polymer solutions containing 0.3% Carbopol with varying concentrations of HPMC. Curve A, B, and C represent 2.0%, 1.5%, and 1.0% HPMC concentrations, respectively. Solid lines represent samples at pH 7.4 and 37° C., and the dashed lines represent samples at 4.0 and 25° C.
Figure 4:
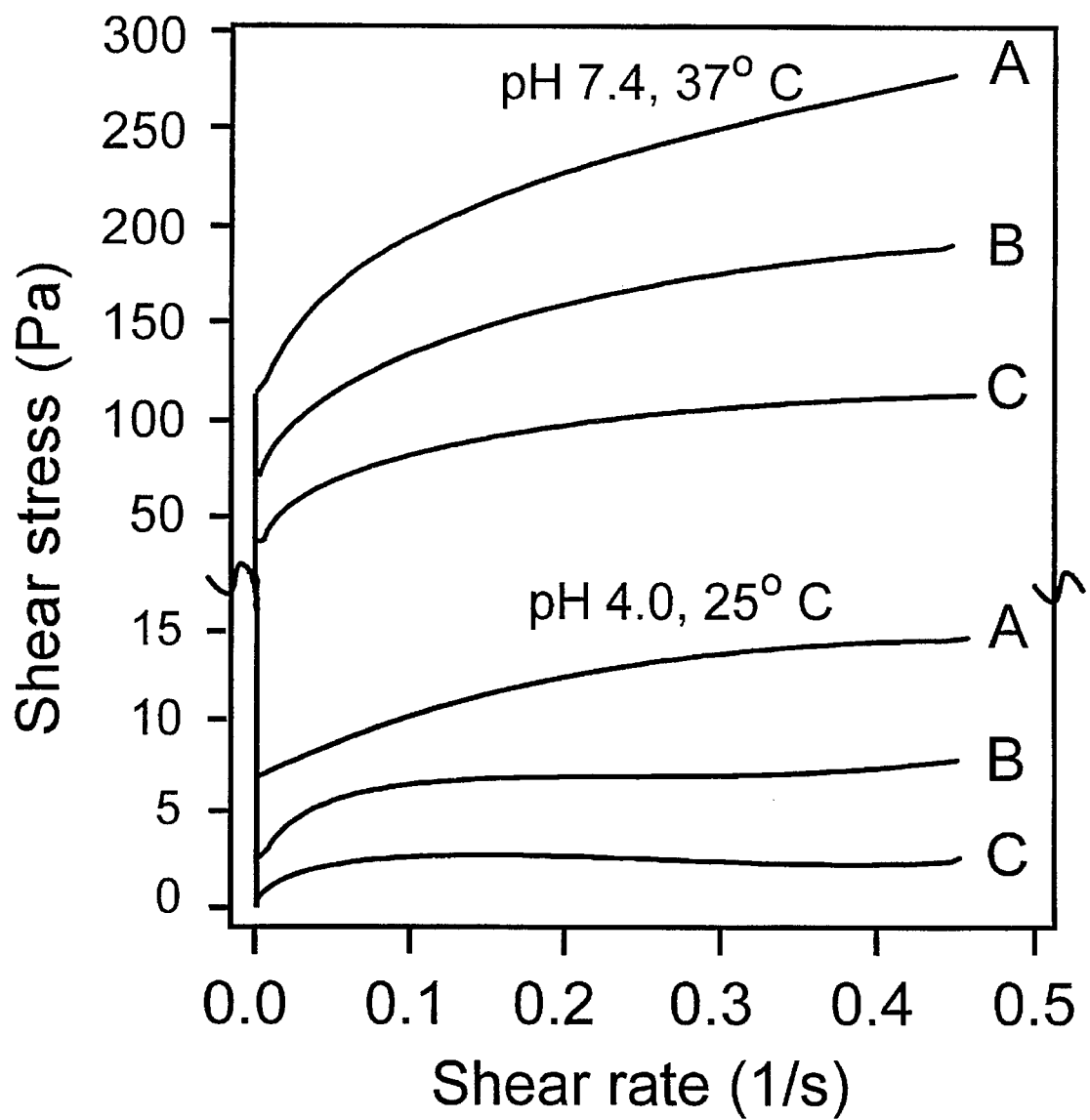
FIG. 4. Shear stress vs. shear rate flow curves of aqueous polymer solutions containing 1.5% HPMC with varying concentrations of Carbopol. Curve A, B, and C represent 0.4%, 0.3%, and 0.2% Carbopol concentrations, respectively.
Figure 5:
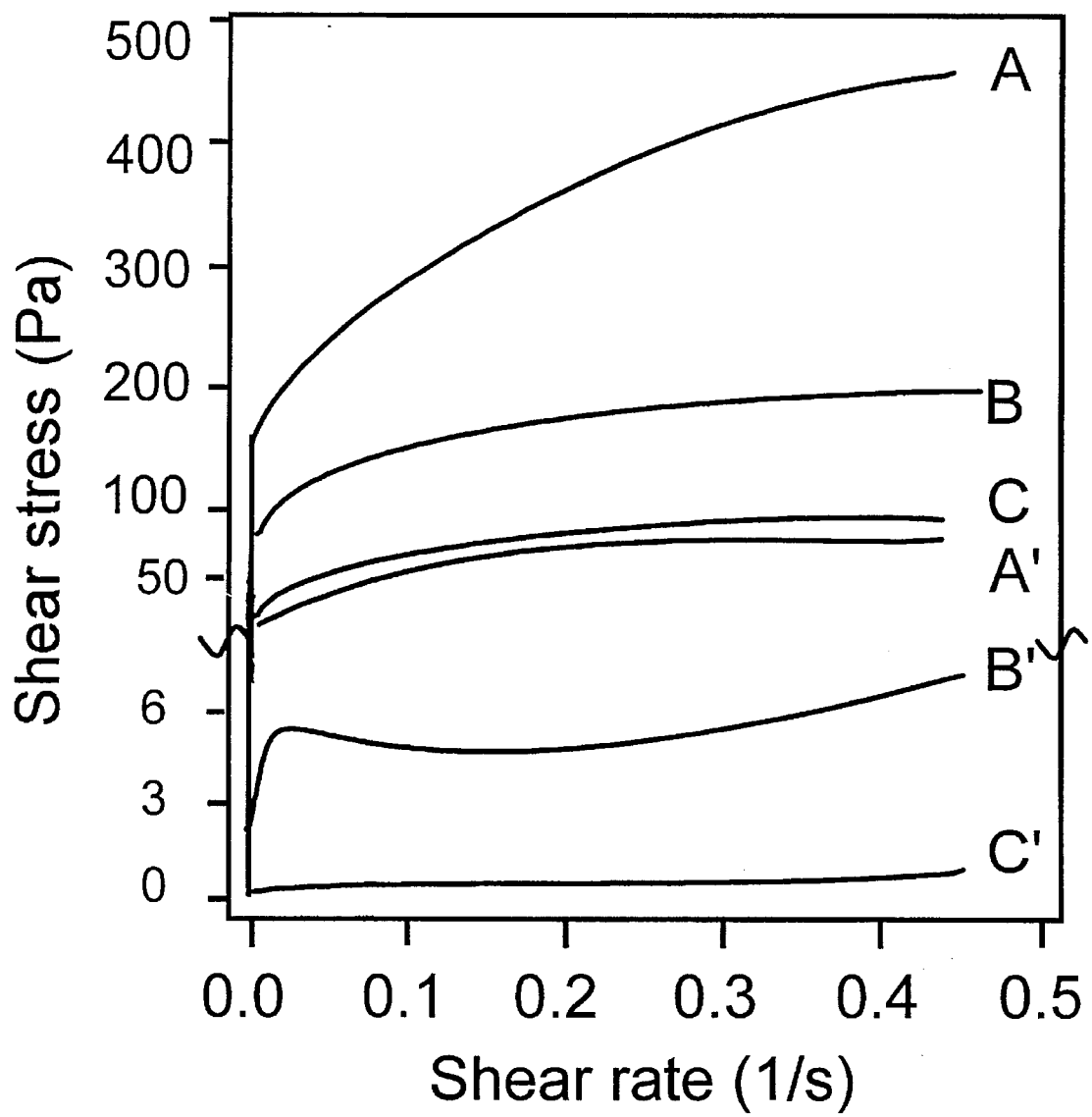
FIG. 5. Flow curves of 1.5% HPMC, 0.3% Carbopol aqueous solutions prepared using HPMC of three different average molecular weights. The alphabets A, B, and C represent HPMC average molecular weights of 246 kDa, 86 kDa, and 26 kDa, respectively. The curves followed by alphabets with a prime (A', B', and C') represent samples at pH 4.0 and 25° C., and those with alphabets without the prime (A, B, and C) represent samples at pH 7.4 and 37° C.

FIG. 3 shows the τ vs. D flow curves for solutions containing 0.3% Carbopol with varying HPMC concentrations. Higher τ responses and yield point values are observed with increasing HPMC concentrations, both at pH 4.0 and 25° C. and at pH 7.4 and 37° C. FIG. 4 shows the τ vs. D flow curves for solutions containing 1.5% HPMC with varying Carbopol concentrations. A similar trend of increase in the τ responses and yield point values is seen with increase in Carbopol concentrations in the concentration range examined. FIG. 5 shows the effect of changes in the average molecular weight of HPMC used to prepare the 1.5% HPMC, 0.3% Carbopol solutions on the τ vs. D flow curves. An increase in the average molecular weight of HPMC used in the solution results in an increase in the observed τ response and yield stress. These studies demonstrate that solutions of desirable rheological properties can be prepared by appropriately choosing the concentrations and/or molecular weights of the polymers. Ideally, an in situ gelling delivery system should be a low viscosity, free flowing liquid to allow reproducible administration into the eye as drops, and the gel formed following phase transition should be strong enough to withstand the shear forces in the cul-de-sac and demonstrate long residence times in the eye or in other physiological environments.

The flow properties of any given system can have, in theory, a significant effect on the behavior of that system when instilled into the eye or applied to similar physiological environments. The gels formed by phase transitions of aqueous solutions containing HPMC and Carbopol at concentrations of 1.5% and 0.3%, respectively, and higher, have demonstrated high τ response and yield point values, representing strong three dimensional gel networks. These gels have adequate strength to withstand the low shear forces likely to be encountered in the cul-de-sac of the eye. These gels will not be susceptible to drainage from the eye as seen in the case of ophthalmic solutions, and will have long residence times.

EXAMPLE 2

Release Profile of Timolol Maleate from an Exemplary Reversibly-Gelling Drug Delivery Composition

MATERIALS AND METHODS

Timolol maleate (TM) was purchased from Sigma Chemical Co. (St. Louis). Timolol maleate was added to gels containing HPMC and Carbopol of different compositions such that the final concentration of timolol maleate was 0.1% w/w. Timolol maleate was gently mixed in gels (pH 7.4) and allowed to equilibrate for 24 hours. Flow curves of TM containing gels were compared with those without TM to ensure that the presence of drug at concentrations of 0.1% did not affect the rheological properties of the gels. Different gel samples containing 0.1% TM were filled in small, circular plastic containers (14 mm inner diameter and 8 mm in depth) and were allowed to gel in an incubator at 37° C. for 30 minutes. Care was taken that the gel contained no air bubbles and that the surface was smooth. The containers were then introduced into 30.0 ml distilled, deionized water in a jacketed beaker maintained at 37° C. using a circulating water bath. The release medium was stirred using magnetic stir bars in such a way that the gel surface was not perturbed. Aliquots of 1 ml were withdrawn from the release medium at 0, 1, 3, 7, 11, 15, 19 and 24 hrs, and replaced with 1 ml water each time. At the end of 24 hrs, the contents of the container were thoroughly mixed with the medium until all the remaining polymeric gel were dissolved and a final aliquot was taken. The aliquots were filtered through 0.2 μm syringe filters and subjected to HPLC analysis to determine the TM concentrations. The dilution of the release medium due to replenishment following each aliquot withdrawal was taken into account to calculate the fractional release of TM from the gels.

HPLC Analysis of TM

The method of Podder et al., Exp. Eye Res., 54: 747–757 (1992), was used to assay TM using a Shimadzu HPLC system, which consisted of a solvent delivery module (model LC-600), an auto-injector (SIL-9A), a variable wavelength detector (model SPD-6AV), and an integrator (model CR 501 Chromatopac). Aqueous samples of TM were analyzed on a Sulpelcosil LC-18 (octadecylsilane; 5-μm particle packing; 250 mm×4.6 mm I.D.) reversed-phase column using injection volumes of 25 μl. The mobile phase comprised 40% acetonitrile, 25% solution containing 4% triethylamine (pH 3), and 35% water. The flow rate was 1 ml/min and the detector was set at a wavelength of 294 nm. All analyses were done at ambient temperature with helium-sparged mobile phases. The assay was sensitive to at least 0.625 μg of TM.

RESULTS

Figure 6:
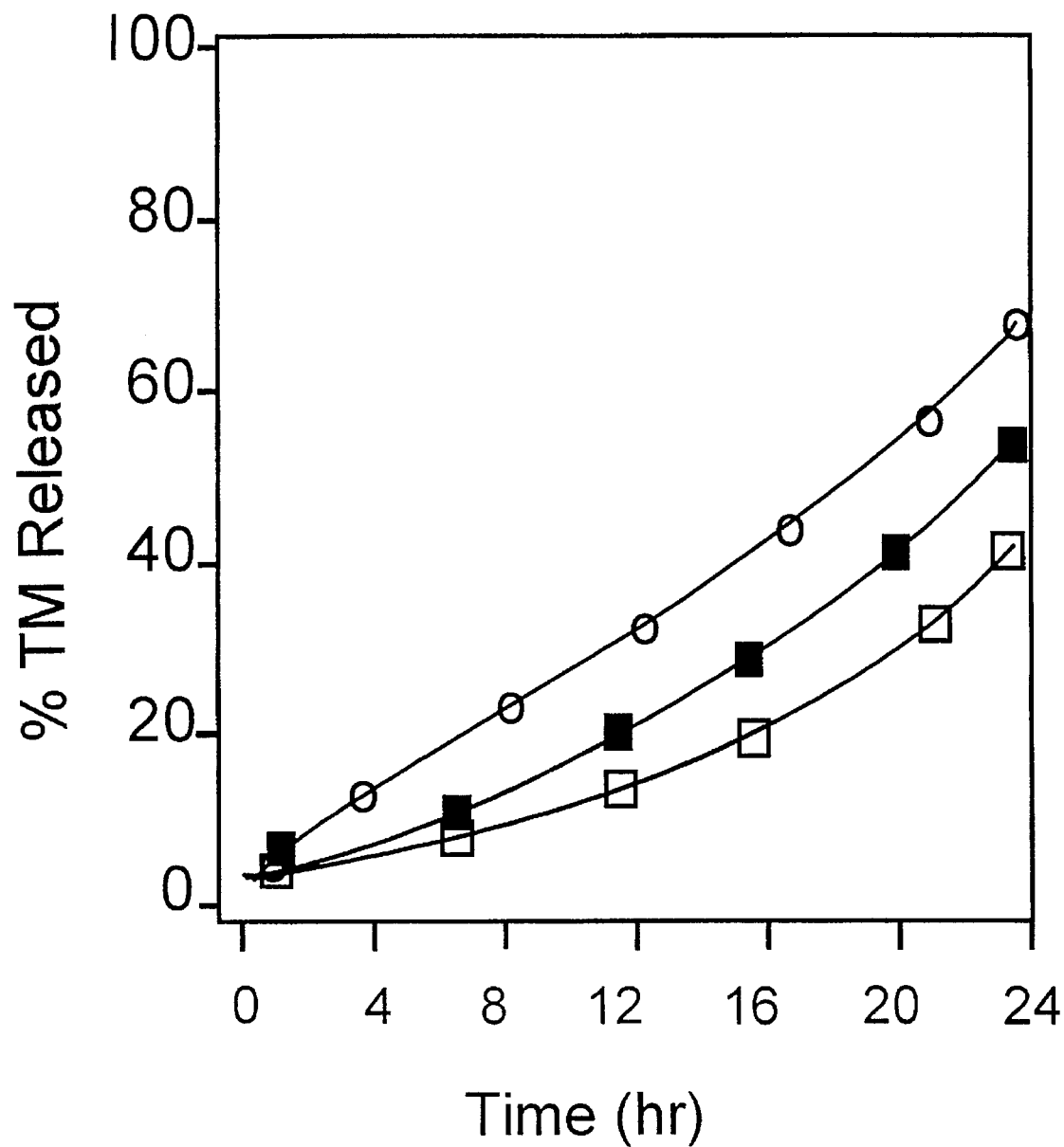
FIG. 6. Effect of change in HPMC concentration on the rate of TM release from gels containing 0.1% TM at pH 7.4. The release profile from gel containing 0.3% Carbopol with 2.0% HPMC (circles), 1.5% HPMC (closed squares), and 1.0% HPMC (open).
Figure 7:
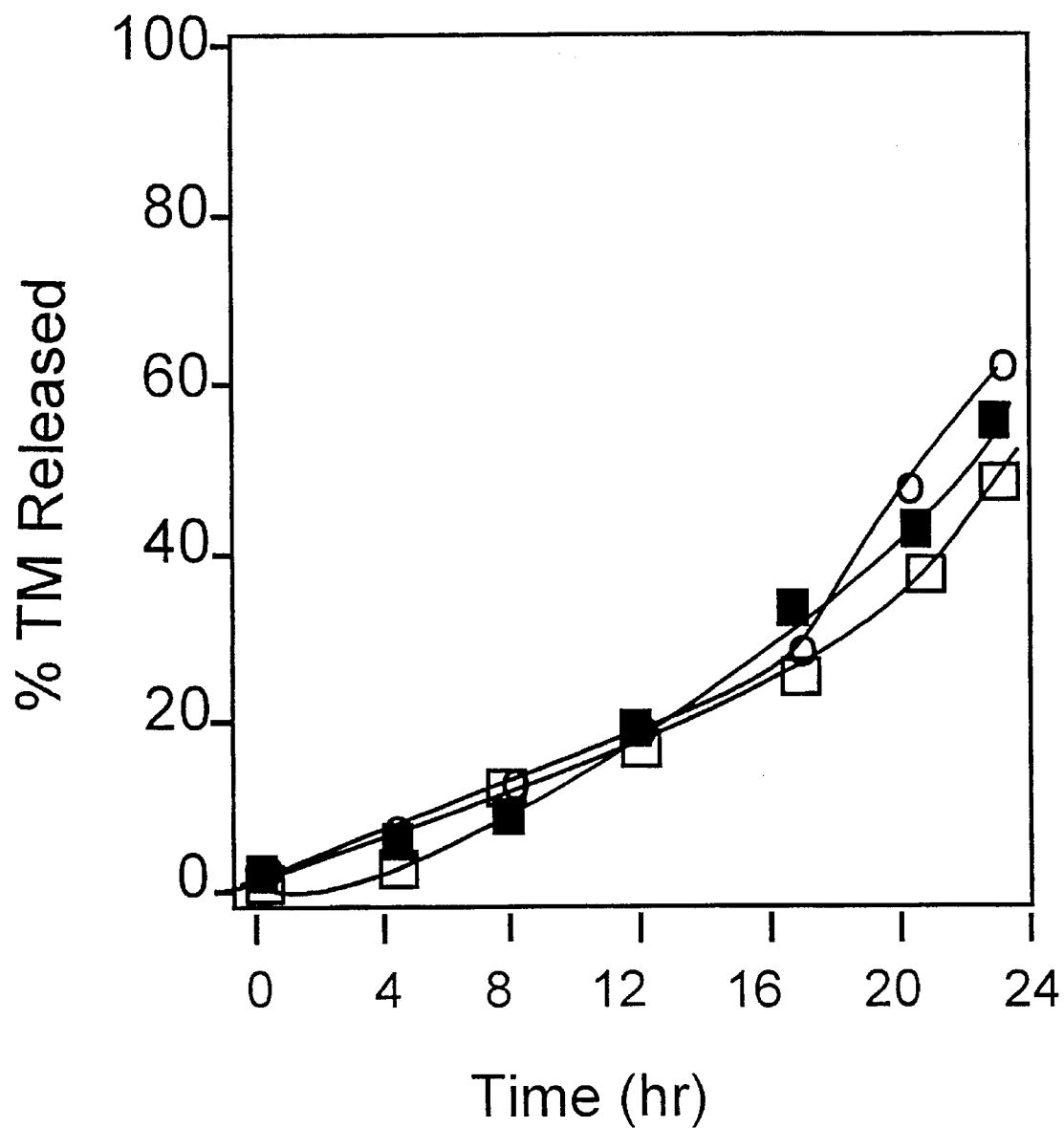
FIG. 7. Effect of change of Carbopol concentration on the rate of TM release from gels containing 0.1% TM at pH 7.4. The release profile from gel containing 1.5% HPMC with 0.4% Carbopol (circles), 0.3% Carbopol (closed squares), and 0.2% Carbopol (open squares).

Experiments were carried out to study the in vitro release profiles of TM from the gels at pH 7.4 and 37° C. FIGS. 6 and 7 compare the fraction TM released from gel containing varying concentrations of HPMC and Carbopol. Focusing first on the exemplary composition of 1.5% HPMC, 0.3% Carbopol (closed squares), the release from the gel is slow and approximately 60% of the total incorporated drug was released during the duration of the study (24 hrs). This demonstrates that the gels have a capacity to release TM in a sustained manner. Periodic visual inspection of the gels in the containers showed that the gels underwent gradual dissolution into the surrounding medium, and that the rate of dissolution decreased as the concentration or the molecular weights of the polymers comprising the gels increased. A similar drug release rate and pattern of dissolution was observed in comparative testing of a temperature/pH-triggered aqueous gelation system comprising 0.3% Carbopol and 1.5% MC. The residence time of the in situ formed gel in the cul-de-sac of the eye is anticipated to be approximately 4–6 hrs, during which time most of the drug will be retained in the gels and the gradual release will occur largely due to the dissolution of the polymeric gels compared to the diffusional release.

Figure 8:
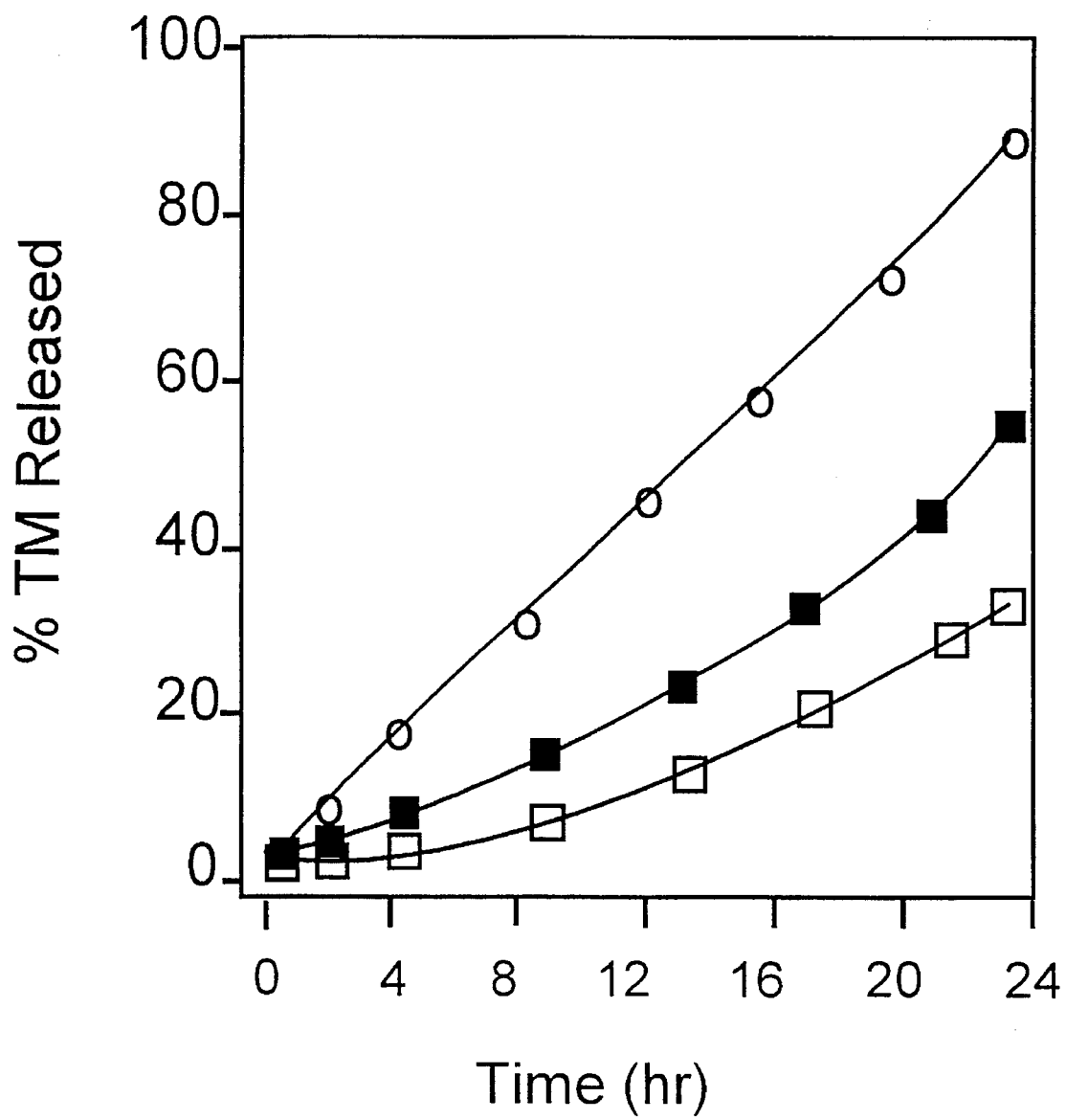
FIG. 8. Effect of change in average molecular weight of HPMC on the rate of TM release from gels containing 0.1% TM at pH 7.4. The release profile from gel containing 0.3% Carbopol, and 1.5% HPMC of average molecular weights of 246 kDa (circles, 86 kDa (closed squares), and 26 kDa (open squares).

The effect of changing the composition of the polymer solution on the release of incorporated TM was also studied. FIG. 6 shows the release profiles of TM from gels containing 0.3% Carbopol with varying HPMC concentrations. A decrease in the rate of release of TM was seen with increasing HPMC concentration. FIG. 7 shows the fraction TM released over time from gels containing 1.5% HPMC with varying Carbopol concentrations. Slight decrease in the rate of release of TM from the gels is observed with increasing Carbopol concentrations. Finally, the effect of changing the molecular weight of HPMC while keeping the total polymer concentration the same is shown in FIG. 8. An increase in the average molecular weight of the HPMC substantially decreased the rate of TM release. The data suggests that considerable changes in the release rate of incorporated drugs can be achieved by changing the composition of the delivery system.

While certain embodiments of the present invention have been described and/or exemplified above, various other embodiments will be apparent to those skilled in the art from the foregoing disclosure. The present invention is, therefore, not limited to the particular embodiments described and/or exemplified, but is capable of considerable variation and modification without departure from the scope of the amended claims.

What is claimed is:

1. A reversibly gelling composition for sustained delivery of a therapeutic or diagnostic agent, said composition exhibiting a reversible increase in viscosity in response to variation in pH over a pre-determined range, said composition comprising an aqueous solution including about 0.01% to 10.0% (w/w) of at least one pharmaceutically acceptable pH-responsive gelling polymer and about 0.01% to 20.0% (w/w) of at least one other pharmaceutically acceptable thermally nonresponsive polymer.

2. The composition of claim 1, which exhibits a reversible increase in viscosity in response to increasing pH.

3. The composition of claim 2, wherein said at least one pH-responsive gelling polymer comprises acidic groups.

4. The composition of claim 3, wherein said pH-responsive gelling polymer is a carboxy vinyl polymer of monomers selected from the group consisting of acrylic acid, alkylacrylic acids, cycloalkylacrylic acids, arylacrylic acids and alkylcrotonic acids.

5. The composition of claim 1, which exhibits a reversible increase in viscosity in response to decreasing pH.

6. The composition of claim 5, wherein said pH-responsive gelling polymer comprises basic groups.

7. The composition of claim 6, wherein said pH-responsive gelling polymer is selected from the group consisting of amino derivatives of polyacrylate and polyalkylacrylates.

8. The composition of claim 1, wherein said other polymer is a thermally nonresponsive hydroxyalkyl cellulose.

9. The composition of claim 8, wherein said other polymer is hydroxypropylmethylcellulose.

10. The composition of claim 2, wherein said pH-responsive gelling polymer is polyacrylic acid and said other polymer is hydroxypropylmethylcellulose.

11. The composition of claim 10, wherein said aqueous solution comprises about 0.05–2.0% (w/w) polyacrylic acid and about 0.05–5.0% (w/w) hydroxypropylmethylcellulose.

12. The composition of claim 11, wherein said aqueous solution comprises about 0.3% (w/w) polyacrylic acid and about 1.5% (w/w) hydroxypropylmethylcellulose.

13. The composition of claim 1, which further comprises a salt in an amount effective to modify the viscosity of said aqueous solution.

14. The composition of claim 13, wherein said salt is present in a salt to polymer ratio of about 0.001 to 0.5.

15. The composition of claim 1, which further comprises an effective amount of a therapeutic or diagnostic agent.

16. A pharmaceutical composition that includes:
   a) a pH-responsive reversibly gelling delivery vehicle comprising an aqueous solution including about 0.01% to 10.0% (w/w) of at least one pharmaceutically acceptable pH-responsive gelling polymer and about 0.01% to 20.0% (w/w) of at least one other pharmaceutically acceptable thermally nonresponsive polymer; and
   b) an effective amount of a therapeutic or diagnostic agent.

17. A pharmaceutical composition as claimed in claim 16, wherein said therapeutic or diagnostic agent is selected from the group consisting of analgesics, anesthetics, antiarthritics, antiinflammatory substances, antiasthmatics, antibacterials, anticoagulants, anticonvulsives, antidepressants, antidiabetics, antifungals, antihistaminics and decongestants, antihypertestive compounds, antiparasitics, antipsychotics, antivirals, carbonic anhydrase inhibitors, antineoplastics, immunosuppressive agents, miotics, anticholinergics, muscle relaxants, mydriatics, nucleic acids and oligonucleotides, ophthalmic agents, peptides and proteins, contrast agents, dyes, fluorescent compounds, radiotracers and lubricating agents.

18. A pharmaceutical composition as claimed in claim 17, wherein said therapeutic or diagnostic agent is an ophthalmic agent.

19. A pharmaceutical composition as claimed in claim 18, wherein said ophthalmic agent is selected from the group consisting of anti-glaucoma substances, dyes, fluorescent compounds, epinephrine, thereof, hyperosmotic agents, lubricating agents, substances for determining pupillary response, antibacterials, antifungals, antivirals, anti-inflammatory agents, analgesics, nucleic acids, oligonucleotides, peptides and proteins.

20. A pharmaceutical composition as claimed in claim 17, which is formulated as an eye drop.

21. A method for sustained delivery of a therapeutic or diagnostic agent to a patient, said method comprising administering to said patient a pharmaceutical composition that includes an effective amount of said therapeutic or diagnostic agent, disposed within a pH-responsive reversibly gelling delivery vehicle comprising an aqueous solution including about 0.01% to 10.0% (w/w) of at least one pharmaceutically acceptable pH-responsive gelling polymer and about 0.01% to 20.0% (w/w) of at least one other pharmaceutically acceptable thermally nonresponsive polymer.

22. A method according to claim 21, wherein said pharmaceutical composition is administered by a route selected from the group consisting of ophthalmic, nasal, oral, otic, topical, rectal, vaginal and urinary tract.

* * * * *